United States Patent [19]

Brassel

[11] Patent Number: 5,541,968
[45] Date of Patent: Jul. 30, 1996

[54] CORING MACHINE AND ARRANGEMENT FOR SAMPLING NUCLEAR-CONTAMINATED AND OTHER HAZARDOUS WASTE

[76] Inventor: Gilbert W. Brassel, 13237 W. 8th St., Golden, Colo. 80401

[21] Appl. No.: 377,343

[22] Filed: Jan. 24, 1995

[51] Int. Cl.⁶ .................................................. G21C 17/00
[52] U.S. Cl. ..................... 376/245; 376/309; 252/635; 588/3; 588/252
[58] Field of Search ................................. 376/245, 309; 252/635; 588/3, 252; 976/DIG. 385

[56] References Cited

U.S. PATENT DOCUMENTS

| | | | |
|---|---|---|---|
| 4,376,392 | 3/1983 | Beitel | 73/864.45 |
| 4,426,888 | 1/1984 | Smith | 73/863.83 |
| 5,238,583 | 8/1993 | Fortson | 210/751 |
| 5,259,697 | 11/1993 | Allen et al. | 405/129 |
| 5,435,176 | 7/1995 | Manchak, III | 73/151 |

*Primary Examiner*—Charles T. Jordan
*Assistant Examiner*—Meena Chelliah
*Attorney, Agent, or Firm*—Millen, White, Zelano, & Branigan, P.C.

[57] ABSTRACT

The core samples of solidified hazardous waste, such as nuclear waste, are extracted from waste material in a drum by inserting rotating tubular core drills into the waste material and then withdrawing the core drills with core samples of the waste material accumulated within the core drills. Preferably, the core samples are retained within plastic tubular retainers which are withdrawn from the core drills and capped. While the rotating tubular core drills are being inserted into the sample, pressurized gas is applied through are annular space between the tubular sample retainers and the walls of the core drills to cool the cutting heads and to expel cuttings away from the end of the drills up to the top surface of the material. In addition, the pressurized gas serves to keep contaminants off the outside surface of the plastic tubular sample containers. If necessary, vacuums can be applied to the plastic tubular retainers in order to retain the core material therein while the core drills are extracted from the waste material in the barrel.

20 Claims, 5 Drawing Sheets

CORING MACHINE AND ARRANGEMENT FOR SAMPLING NUCLEAR-CONTAMINATED AND OTHER HAZARDOUS WASTE

FIELD OF THE INVENTION

The present invention relates to a coring machine and arrangement for sampling nuclear-contaminated and other hazardous waste. More particularly, the present invention is directed to a coring machine and arrangement for sampling solidified, nuclear-contaminated and other hazardous waste wherein the coring machine and arrangement are configured for obtaining sample cores from the full depth of the waste filling a drum.

BACKGROUND OF THE INVENTION

During the past several decades, hazardous waste and nuclear waste has been, in many situations, solidified in barrels and disposed of by being placed in the ground in landfills. Today, regulatory requirements mandate that such waste be extensively characterized to demonstrate compliance with all of the waste acceptance criteria of an accepting disposal site. Such characterization must show the waste to be in full compliance with the regulated physical, chemical and radiological characteristics permitted by the disposal facility. Thus, it is frequently necessary to be able to check the state of waste materials, such as nuclear waste materials, throughout individual drums. To date, no arrangement exists for doing this safely with minimal disturbance of material within the drums, especially if the waste is a solidified material such as a cemented monolith.

SUMMARY OF THE INVENTION

It is a feature of the present invention to provide a new and improved coring machine and to provide a new and improved arrangement for accumulating and retaining core samples of solidified nuclear and/or hazardous waste materials.

The present invention is directed to an arrangement for acquiring a core sample of such waste material. The arrangement comprises a tubular core drill having a hollow core and a bit at one end for coring into the material to be sampled. The core drill has a selected inner diameter in which a tubular core retainer having an outside diameter less than the inside diameter of the core drill is positioned to define an annular space therebetween. Fluid (gas) under pressure is applied to the annular space between the tubular sample retainer and the inner wall of the core drill. The fluid flows down the space and out of the core drill proximate the bit and remove cuttings as the bit penetrates the material. This flow also provides a means of maintaining the outside surface of the tubular core retainer in a near contamination-free condition which is an essential requirement for the subsequent safe handling of the core sample.

In another aspect, the present invention is directed to a machine for sampling solidified waste material within a container wherein the machine comprises a base, a platform for mounting the container on the base and at least one core drill disposed above the platform in initial spaced relation with respect to the top of the container when the container is mounted on the platform. The core drill has a first end with a bit thereon and a second end. A support for mounting the core drill includes a spindle rotatably mounted thereon and attached to the core drill at the second end thereof for rotating the core drill. A motor is provided for rotating the core drill and a lifting device (elevator) is provided for lifting the drum into proximity with the bit of the core drill and providing a seal between the drum and a seal plate. Such an arrangement provides essential containment of hazardous and/or radioactive contaminants during the core sampling operation. A drive lowers the support for the core drill while the core drill is rotating so that the core drill penetrates solidified waste material within the drum and accumulates a core sample of the material solidified within the hollow tubular sample container within the core drill. The drive thereafter raises the core drill to withdraw the core drill from the solidified waste material with a core sample therein, A tube is disposed within the core drill for retaining the core sample and for safely removing the core sample from the core drill for subsequent processing.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
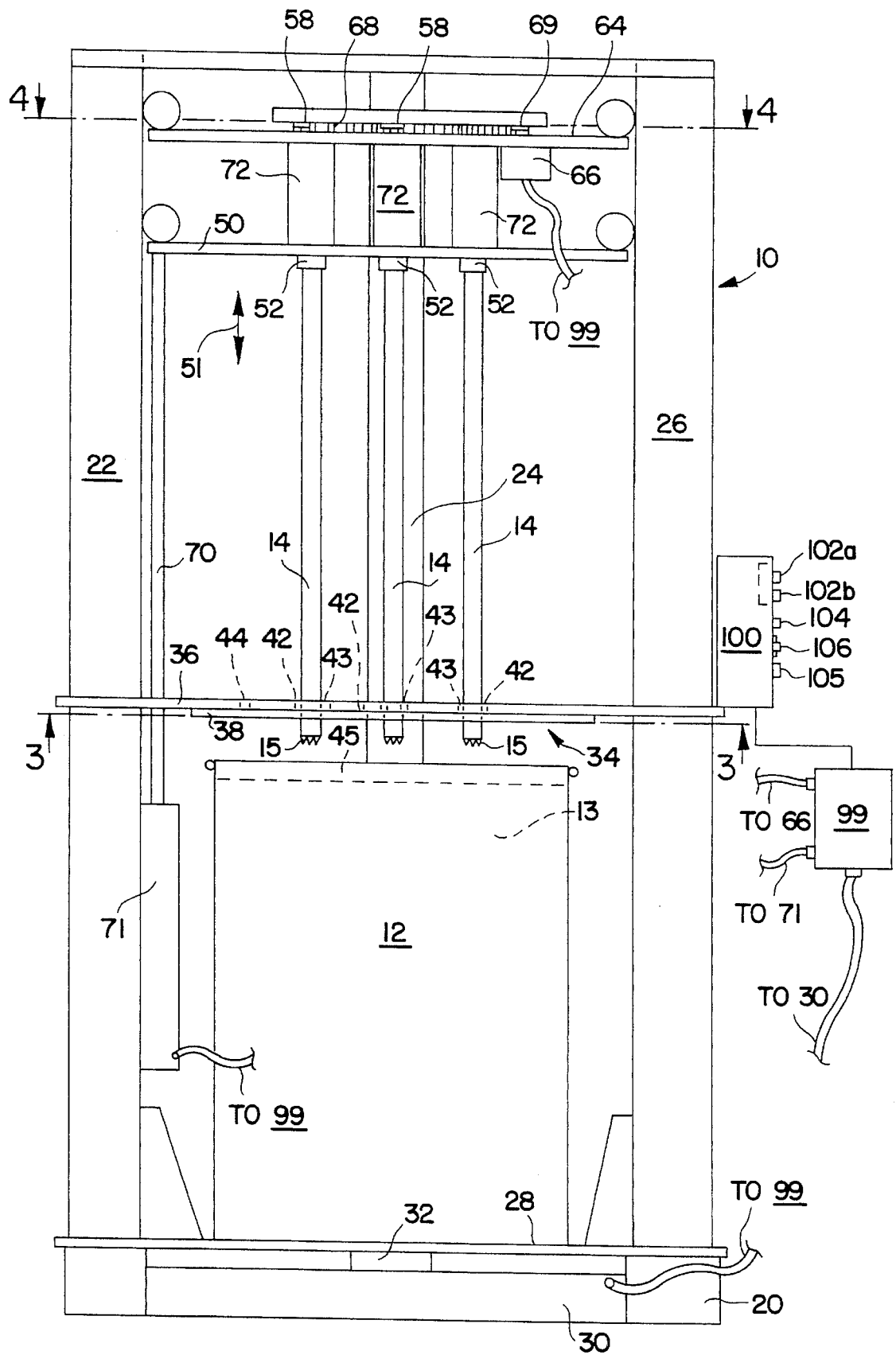
FIG. 1 is a side view of a machine configured in accordance with the principles of the present invention showing the position of core drills prior to the insertion into the drum of solidified waste material.
Figure 2:
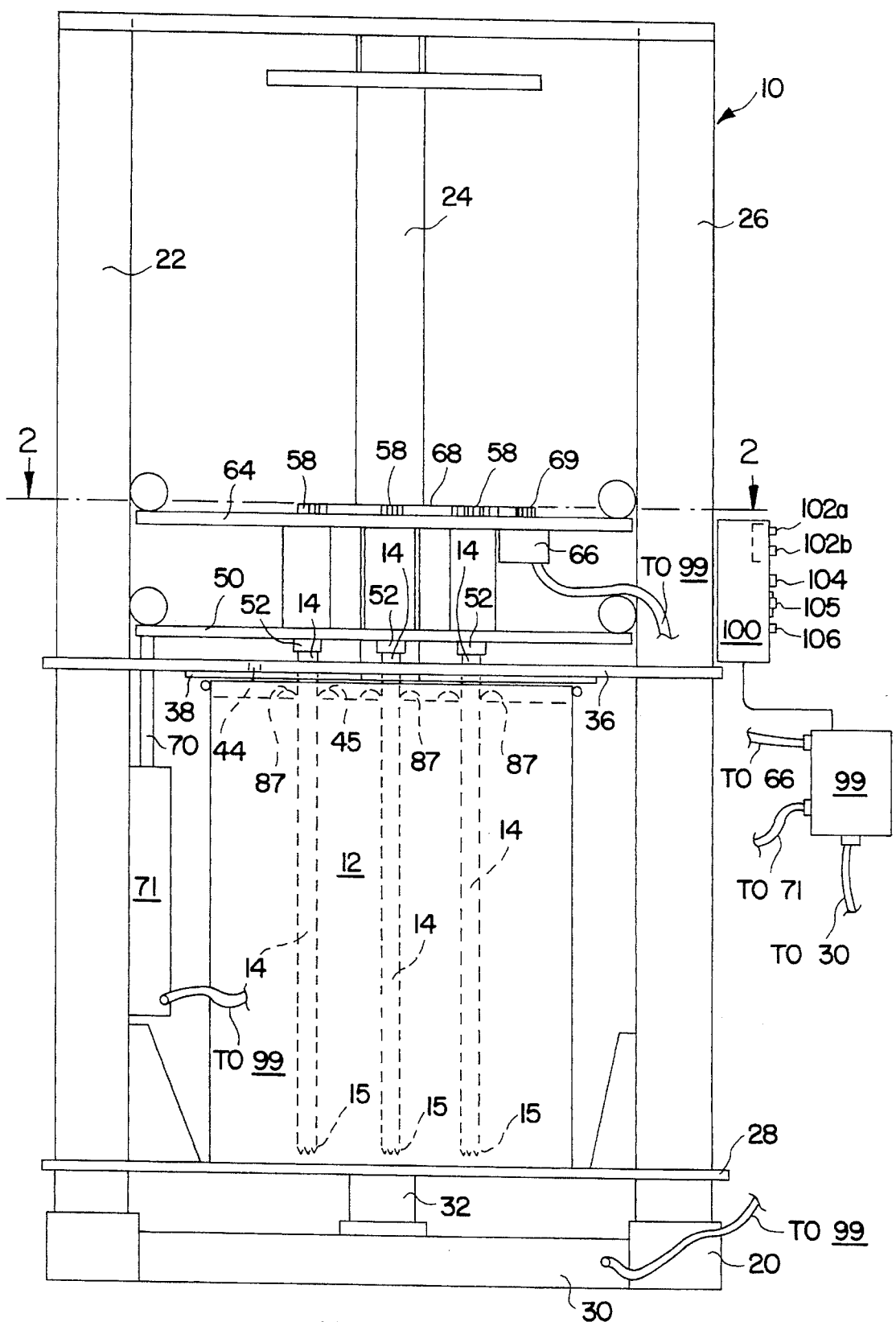
FIG. 2 is a view similar to FIG. 1 but showing core drills inserted into the drum.

Referring now to FIGS. 1 and 2, there is shown machine 10 configured in accordance with the principles of the present invention for sampling the solidified waste 13 of a drum 12, such as a 55 gallon drum, with three core drills 14, spaced 120° apart and having bits 15. The waste contents 13 of the drum 12 may include nuclear contaminated and/or other hazardous solidified waste and may be in the form of a cemented monolith. The machine 10 includes a base 20 and three support columns 22, 24 and 26 which are spaced 120° apart. Mounted on the base 20 is a platform 28 upon which the drum 12 rests.

The platform 28 is raised from the FIG. 1 position to the FIG. 2 position with respect to the base 20 by a pneumatic/hydraulic lifting mechanism 30 which, for example, might project a piston 32 therefrom to lift the barrel 12. Alternatively, the platform 28 may be raised by hydraulic cylinders fixed to the columns 22, 24 and 26 wherein the cylinders have piston rods attached to the columns which pull the platform 28 upwardly. In this way, a gap 34 which allows the drum 12 to be disposed between the platform 28 and a seal plate 36 is closed.

Figure 3:
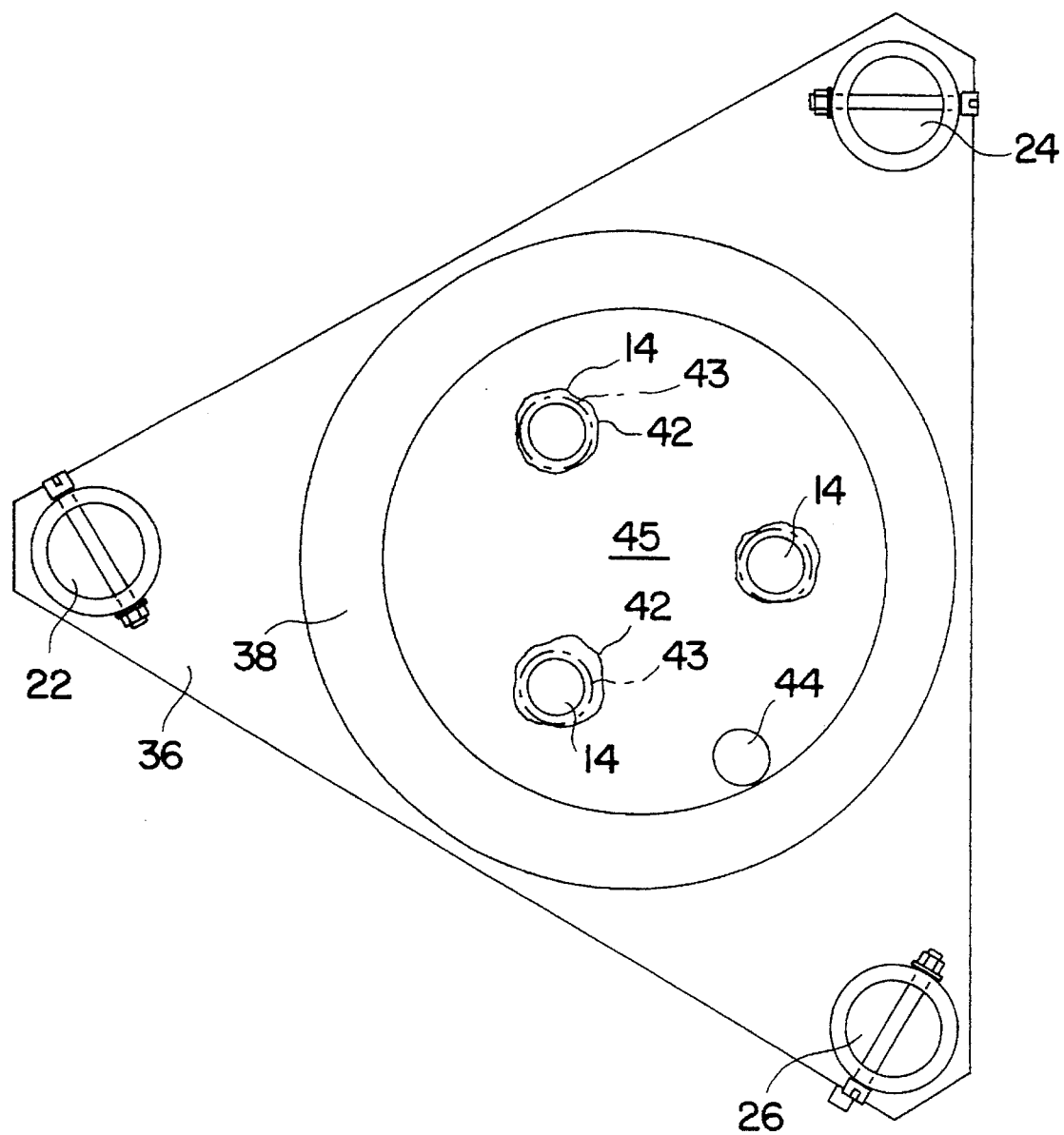
FIG. 3 is a top view of the machine of FIGS. 1 and 2 taken along lines 3—3 of FIGS. 1 and 2.

As is seen in FIG. 3, the seal plate 36 has a gasket 38 thereon which has an outside diameter greater than, and an inside diameter less than, the diameter of the drum 12 for sealing with the top of the drum. The seal plate 36 also has radially sealed circular openings 42 through which the core drills 14 pass.

In order to enhance sealing between the plate 36 and the core drills 14, each core drill has a split seal 43 inserted in the circular opening 42 so that air, which may include particles (cuttings) of the waste material 13 from the drum 12, does not escape between the core drill and circular opening. A vacuum line 44 may also be connected to an annular space 45 defined by the inner diameter of the gasket 38 to draw off air suspended particles (cuttings) of the waste material 13. The air drawn through line 44 is filtered in a separate high efficiency particulate air (HEPA) filter system.

Core drills 14 are journaled in a support plate 50 for rotation with respect to the support plate and for axial translation in an axial direction 51 upon moving the support plate 50 downwardly from the FIG. 1 to the FIG. 2 position. Mounted on the support plate 50 are spindles 52 which are used to rotate the core drills 14.

Figure 4:
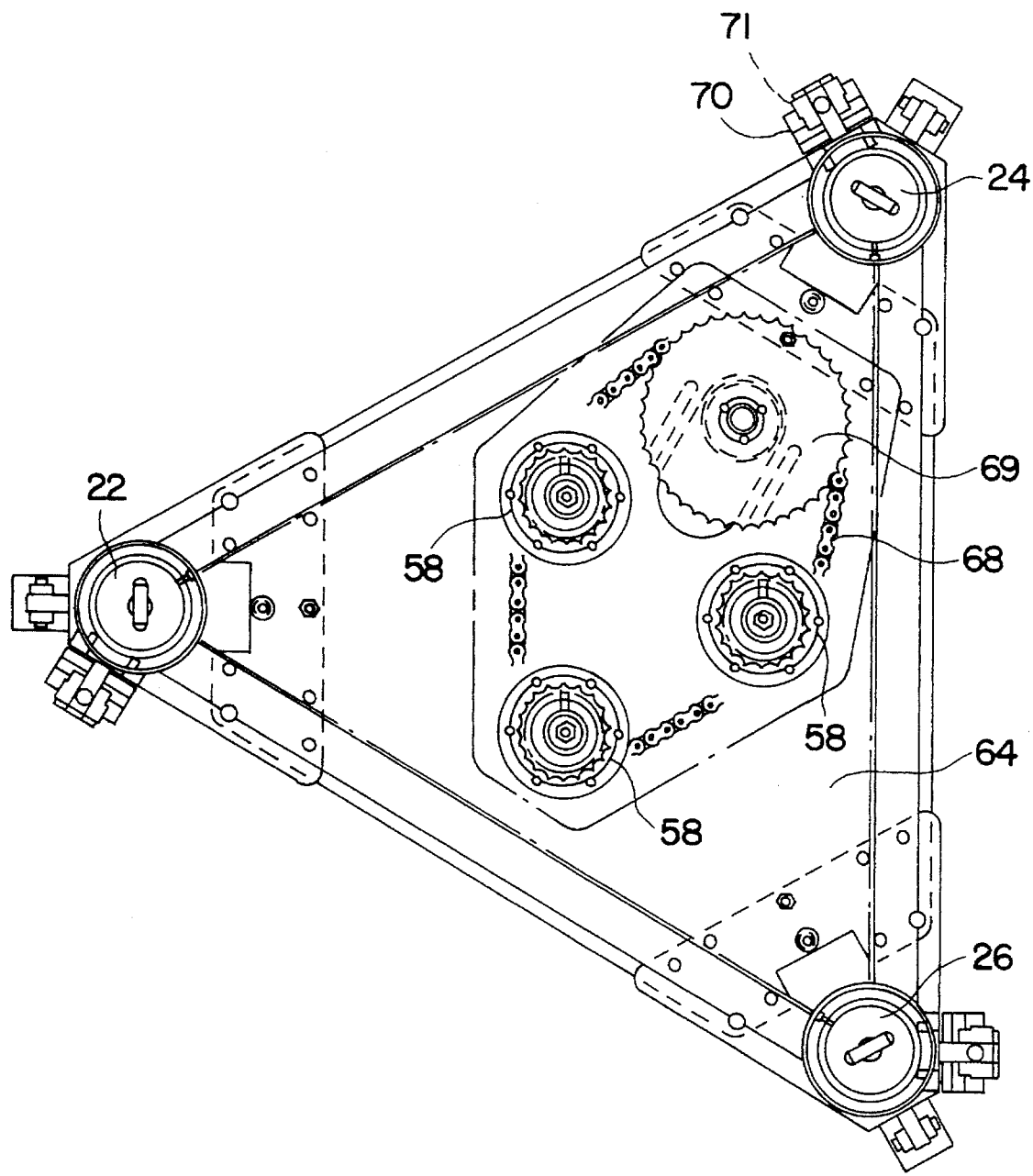
FIG. 4 is a sectional view of the machine of FIGS. 1 and 2 taken along lines 4—4 of FIGS. 1 and 2.

As is seen in FIG. 4 in combination with FIG. 1, the spindles 52 each have sprockets fixed to the top or second ends thereof on opposite sides of a mounting plate 64. The sprockets 58 are driven by a hydraulic motor 66 that drives a chain 68 trained around the sprockets with a drive sprocket 69.

Referring now to FIGS. 1 and 2, it is seen that the plates 50 and 64 are rigidly associated with one another and are raised and lowered together by three piston rods 70 (only one of which is shown) spaced 120° apart and projected and retracted by hydraulic cylinders 71 (only one of which is shown) which are fixed with respect to the supporting columns 22, 24 and 26. While the plates 50 and 64 are being lowered to the FIG. 2 position, the core drills 14 rotate cutting into the waste material 13 in order to obtain core samples. The core drills 14 do not need to be rotated while the plates 50 and 64 are being raised.

Figure 5:
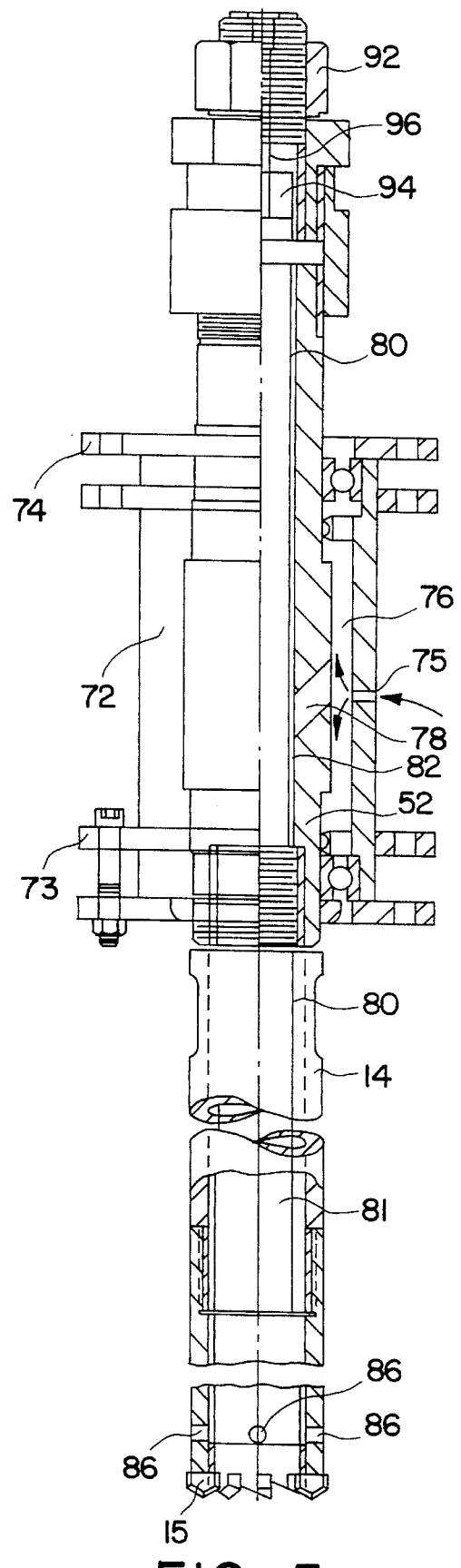
FIG. 5 is a side view partially in section showing a tubular insert within a core drill, the core drill and insert configured to operate in accordance with the principles of the present invention.

Referring now to FIG. 5, where a core drill 14 and spindle assembly is shown, it is seen that each of the core drills 14 are threaded into the ends of the spindles 52. The spindles 52 are each mounted in housings 72 and the housings are secured to the support plates 50 and 64 by flanges 73 and 74, respectively. Each of the housings 72 has a port 75 through which pressurized gas is applied. The port 75 communicates with an annular chamber 76 which in turn communicates with a second port 78 through the wall of the core drill 14.

The core drill 14 is hollow and receives therein a plastic core retaining tube 80 that is coaxial with the core drill. The plastic core retaining tube 80 retains a core sample 81 of the solidified waste material 13 in the drum 12 as the core drill 14 penetrates the waste material. There is a small annular space 82 between the outer surface of the tube 80 and the inner wall 83 of the core drill 14. Pressurized gas, applied through the bore 75, flows down the small space 82 between the plastic sample tube 80 and the wall 83 of the core drill 14 and out of radial openings 86 proximate the bit 15 at the free end of the core drill. Gas flowing out of the radial openings 86 causes cuttings 87 (see FIG. 2) to be forced away from the bit and up the outside surface 88 of the core drill 14. The cuttings 87 accumulate at the top of the holes in the material 13 being cored so as to form "ant hills" around the top of holes as the holes are being drilled in the material. Additionally, the gas flow cools the cutting bit 15, and serves to minimize contamination of the outside surface of the plastic core retaining tube 80.

At the top of each spindle 52, there is disposed a nut 92 which has an annular fitting 94 which is received in the end of the plastic core retaining tube 80. If necessary, a vacuum may be applied through an axial port 96 in the nut 92 to ensure that the core sample material 81 within the tube 80 is maintained inside of the tube when the core drills 14 are withdrawn from the barrel.

The controls, which operate the machine 10 by applying hydraulic fluid from a hydraulic power supply 99, are located in part on the machine and in part in a control box 100. The control 102 for raising and lowering the drum 12 is attached To one side of the machine. This control activates the lifting mechanism 30. The controller includes controls for all other machine operations, including: a button 104 for starting and stopping the hydraulic power supply; a control 105 for starting, stopping and adjusting the speed of the hydraulic motor 66 which drives the core drills 14; and a control 106 which causes the hydraulic cylinders 71 to retract and extend the piston rods 70 as well as setting the speed of these retraction and extension operations, for raising and lowering the drill cores 14.

In operation, a drum 12 is loaded onto the platform 28 with a forklift (not shown) or some other conveying and loading device. The drum-up control 102a is then activated to raise the drum so that the top of the drum seals against the gasket 38. A hydraulic power supply is then energized by pushing the start button 104. Activation of the control 105 energizes the motor 66 which causes the spindles 52 to rotate within the spindle housings 72 at a variable speed, depending upon the setting of the control 105.

Gas pressure is then applied to the port 75 so as to cause a stream of gas to flow in the passage 82 and out of the holes 86 in the bottom of the core drills 14. By activation of control 105, the core drills 14 are then simultaneously advanced axially hydraulically by pulling the piston rods 70 into the hydraulic cylinders 71. Control 105 permits the operator to adjust the speed of this function. Since the bits 15 at the end of the core drills 14 are rotating, the core drills cut their way into the solidified waste material 13.

As the waste material is cut, it is formed into the cores 81 which are received in the plastic core sample tubes 80 (see FIG. 2). Once the drill bits 15 of the core drills reach the lower part of the drum 12, rotation of the motor 66 is stopped, preferably by a limit switch. The control 102b is then operated again to cause the mounting platforms 50 and 64 to rise, thus pulling the core drills 14 (containing core samples 81) from the material 13 in the drum 12. As this is done, a vacuum may be applied if needed through the ports 96 in the nuts 92 of the core drills 14 to retain the core samples 81 within the plastic sample retaining tubes 80.

The threaded plugs 92 are then removed from the core drills 14 so that the core tubes 80 with the samples 81 therein may be withdrawn from the core drills. The ends of the core sample tubes 80 are then capped with plastic caps so that the core samples 81 of the waste material 13 therein are retained for analysis.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A machine for sampling a monolithic solidified material within a container, the machine comprising:
   a base;
   a platform for mounting the container on the base;
   at least one rotatable core drill disposed above the platform in initial spaced relation with respect to the top of the container when the container is mounted on the platform, the core drill having a first end with a bit thereon for cutting the monolithic solidified material and a second end;

a support for mounting the core drill, the support including a spindle rotatably mounted thereon and attached to the core drill at the second end thereof for rotating the core drill;

a motor for rotating the core drill;

a device for lifting the drum into proximity with the bit on the core drill;

a seal proximate the bit for sealing the upper lip of the waste container with a seal plate when the drum is lifted into proximity with the bit;

a drive for lowering the support for the core drill while the core drill is rotating wherein the core drill penetrates the monolithic solidified material within the drum and accumulates the material within the hollow core of the core drill, the drive thereafter raising the core drill to withdraw the core drill from the material with a core sample therein; and a separate tubular core retainer coaxially disposed within the core drill for retaining the sample therein and for shielding the surrounding environment from direct contact with the core sample after the core sample has been removed from the core drill for subsequent processing.

2. The machine of claim 1, wherein the tubular core retainer within the core drill comprises a tube having an outside diameter less than the inside diameter of the core drill and wherein the machine further includes a pressurizer for applying fluid pressure in the space between the tube and core drill for displacing cuttings generated as the bit end of the core drill removes material cools the cutting bit and serves to minimize contamination of the outside surface of the plastic core retaining tube.

3. The machine of claim 2, wherein the fluid pressure is applied by pressurized gas.

4. The machine of claim 3 further including an opening in the end of the core drill for applying a vacuum thereto to retain material in the core tube.

5. The machine of claim 1, wherein there are a plurality of core drills extending from the support.

6. The machine of claim 5, wherein the plurality of core drills are driven for rotation by a single drive, the drive itself being driven by the motor.

7. The machine of claim 6, wherein the drive for the core drill comprises a chain or belt which engages sprockets fixed to the spindles attached to the second ends of the core drills.

8. The machine of claim 1 further including a controller positioned remotely with respect to the core drill.

9. The machine of claim 1, wherein the container is a waste drum.

10. The machine of claim 1, wherein the container is a drum and wherein there are three core drills mounted for simultaneously sampling the solidified waste material in the drum.

11. The machine of claim 10, wherein the solidified waste material in the drum is nuclear-contaminated or other hazardous waste.

12. An arrangement for acquiring a core sample of a monolithic solidified waste material comprising:

a tubular core drill having a hollow core and a bit at one end for cutting into a solidified waste material to be sampled, the core drill having a selected inner diameter;

a tubular core retainer removable from the tubular core drill and having an outside diameter less than the inside diameter of the core drill to define a space therebetween when coaxially positioned within the core drill; and a source of pressure for applying fluid under pressure to the annular space between the tubular core retainer and the inner wall of the tubular core drill wherein fluid flows down the space and out of the core drill proximate the bit thereof to remove cutting debris from the surface of the tubular core retainer as the bit penetrates the waste material.

13. The arrangement of claim 12, wherein the fluid is a gas.

14. The arrangement of claim 13, wherein a motor rotates the core drill as it is advanced into the waste material.

15. The arrangement of claim 13, wherein the core drill has radial openings therein inboard of the bit for allowing the gas to flow from the bit.

16. The arrangement of claim 15, wherein the gas is air or inert gas.

17. The arrangement of claim 12, further including an opening in communication with the core sample retaining tube for applying a vacuum thereto to retain the core sample within the tubular core retainer as the drill bit is removed from the material.

18. The arrangement of claim 17, wherein the material is solidified nuclear-contaminated or hazardous waste and is retained within a container, the arrangement further including a seal for sealing the container from the environment, and a seal surrounding the core drill.

19. The arrangement of claim 12, wherein the material is solidified nuclear contaminated or hazardous waste configured as a monolithic and is retained within a container, the arrangement further including a seal for sealing the container from the environment, the seal surrounding the core drill.

20. The arrangement of claim 19, wherein the material is in the form of a cemented monolith.

* * * * *